United States Patent [19]

Lewis et al.

[11] Patent Number: 5,834,492
[45] Date of Patent: Nov. 10, 1998

[54] WATER SOLUBLE ORALLY EFFECTIVE IRON CHELATOR

[75] Inventors: Neil Lewis; Vithal Patel, both of Plainsboro; Jacek Terpinski, North Brunswick; Robert Bliss, Edison, all of N.J.

[73] Assignee: Jacobus Pharmaceutical Co., Princeton, N.J.

[21] Appl. No.: 765,369

[22] PCT Filed: Jul. 10, 1995

[86] PCT No.: PCT/US95/08519

§ 371 Date: Apr. 7, 1997

§ 102(e) Date: Apr. 7, 1997

[87] PCT Pub. No.: WO96/02531

PCT Pub. Date: Feb. 1, 1996

[51] Int. Cl.$^6$ .................. C07D 401/02; A61K 31/44
[52] U.S. Cl. ............................ 514/335; 546/261
[58] Field of Search .............................. 546/261; 514/335

[56] References Cited

U.S. PATENT DOCUMENTS 2,810,725 10/1957 Bernstein ............................. 546/261

*Primary Examiner*—Zinna Northington Davis
*Attorney, Agent, or Firm*—Omri M. Behr, Esq.

[57] ABSTRACT

There is provided a synthesis and description of diprotonated diacid derivatives of pyridoxal isonicotinoyl hydrazone (PIH) of formula (I), wherein q is 1 or 2, DPA is 2 mols of a monoprotic acid HX or 1 mol of a diprotic acid $H_2Y$ wherein X is a monovalent anion and Y is a divalent anion and both HX and $H_2Y$ are pharmaceutically acceptable acids. The unique properties of the PIH.DPA molecule make it particularly suitable and pharmaceutically acceptable for formulation as an oral dosage form by virtue of its ready solubility in water. There are further provided methods of utilizing such chemically unique and isolable crystalline compounds, such as PIH.2HCl, as a pharmaceutical chelator. There are further provided pharmaceutical formulations specifically for the reduction of iron overload, and related chelatable metals, in subjects susceptible to such overload.

21 Claims, 8 Drawing Sheets

WATER SOLUBLE ORALLY EFFECTIVE IRON CHELATOR

This application is a 371 of PCT/US95/08519, filed Jul. 10, 1995.

BACKGROUND OF THE INVENTION

1. Field of the Invention

This invention relates to the synthesis, isolation and novel pharmaceutical formulation of a chemically distinct and pharmaceutically unique class of compounds, namely pyridoxal isonicotinoyl hydrazone polyprotic salts, that have heretofore been unattainable due to the complex chemical characteristics of the free base precursor, pyridoxal isonicotinoyl hydrazone (PIH). These compounds are generally crystalline and generally free of associated water. The solubility and stability properties of these salts makes them particularly suitable as orally administered chelators that can complex and remove pharmacologically significant levels of iron at dosages that are pharmaceutically meaningful.

2. Discussion of the Prior Art

The synthesis of pyridoxal isonicotinoyl hydrazone (PIH; 3-hydroxy-5-hydroxy- methyl-2-methyl-4-pyridinylcarboxaldehyde 4' pyridinecarboxylic acid hydrazone) was first reported by Sah in 1953 {P. P. T. Sah, *J. Am. Chem. Soc.* 76:300 (1953)}. The very low water solubility of PIH as a pale yellow solid was noted at that time. There appeared subsequently in the literature evidence of complex behavior of PIH by virtue of its ability to form, under similar synthetic approaches, various hydrates and fractional or monohydrochlorides, all described with similar melting points but differing in their physical appearance.

The varied spectral properties of hydrates and salts reported to date were accompanied by comments about differing and limited water solubilities (S. Avramovici-Grisaru, S. Sarel, G. Link and H. Hershko. *J. Med. Chem.* 26:298–302 (1983).

Literature reports have specifically referred to the dihydrate (D. Libermann, N. Rist, F. Grumbach, M. Moyeux, B. Gauthier, A. Rouaix, J. Maillard, J. Himbert and S. Cals. *Bull. Soc. Chim. Fr.* 1430–43 (1954)), a monohydrate (H. C. Beyerman, J. S. Bontekoe, W. J. Van der Burg and W. L. C. Veer. *Recl. Trav. Chim. Pays-Bas.* 73:109–17 (1954)), (S. Avramovici-Grisaru, supra) the monohydro-chloride hydrate and the 0.5 hydrochloride and the monohydrochloride (J. Webb and M. L. Vitolo, *Birth Defects.* 23 (5B):63–70 (1988)). A patented process for making PIH as the free base (S. Archer and M. E. Auerbach, U.S. Pat. No. 2,775,598; Dec. 25, 1956) in addition to other reported syntheses of PIH required the use of appreciable amounts of water, thus generating complex and often differing products with respect to metal ion chelation, protonation, solvation and compound colors (which can range from white to yellow to green to orange) (T. B. Murphy, N. J. Rose, V. Schomaker and A. Aruffo. *Inorg. Chim. Acta.* 108:183–194 (1985)).

There appears in the patent literature (J. Bernstein, U.S. Pat. No. 2,810,725, Oct. 22, 1957), reference to an intermediate monosulfate from water as an insoluble orange solid which is stated to have been converted to the free base under aqueous conditions. The patent further refers to the conversion of a PIH to monohydrochloride and to the dihydrochloride (Example 6 of the patent). Attempts to repeat this work by applicants has not been successful.

The procedures to form the free base (PIH) as disclosed by Sah supra. have been found operative. Moreover, Archer et al, in U.S. Pat. No. 2,775,598, disclose another procedure for making PIH via a manganous complex which was also found operative, both with respect to production of the intermediate manganous complex and the subsequent conversion to the free base.

It is interesting to note that Example 1 of Bernstein et al supra patent closely parallels, but is not totally identical with the Archer et al supra method which yields the intermediate manganous complex. An attempted repetition of the aforesaid Example 1 by applicants, yielded the Archer manganous complex but not the Bernstein sulfate.

The stability and solubility of the isolated PIH products reported to date, by others, which includes demonstrable interconversion of one form (and color) to another in the presence of moisture and light, made those derivatives of limited utility for development of a reproducible, pharmaceutically acceptable bulk drug that could be incorporated into a reliable and efficacious oral dosage formulation.

Thus the literature covering PIH does not include isolation of crystalline polyprotonated species with favorable properties of biologically significant iron chelation preserved. The description of interconvertible stereoisomers, described as the "E" and "Z" isomers (S. Avramovici-Grisaru, supra), comprising different colored crystals, also raise questions of reproducibility and stability for developing a suitable pharmaceutical product meeting the quality control standards recognized as essential by those skilled in the pharmaceutical sciences.

While ionization curves have been reported for PIH and its iron complexation products across a broad pH range, the titration curves for such studies have only alluded to polyprotonated polycharged species of PIH but have not produced the isolable polyprotonated species as crystalline chemical entities.

(D. R. Richardson, L. M. W. Vitolo, G. T. Hefter, P. M. May, B. W. Clare, J. Webb and P. Wilairat. *Inorgan. Chim. Acta.* 170:165–70 (1990); L. M. W. Vitolo, G. T. Hefter, B. W. Clare and J. Webb. *Inorqan. Chim. Acta.* 170:171–176 (1990)).

Similarly, the solubility characteristics of such crystalline polyprotic polycharged species have not been defined with regard to their potential for efficacious pharmaceutical oral activity despite the recognition that PIH itself was potentially useful as an orally effective chelator, specifically for iron overload.

Similarly, the solubility characteristics and other physical constants of such crystalline discharged species have not been previously reported. Table summarizes some of our findings which define, in part, the potential for water soluble derivatives to demonstrate efficacious pharmaceutical oral activity. Despite the recognition that PIH, as a free base, was potentially useful as an orally effective chelator, specifically for iron overload, its limited water solubility appears to limit its utility in vivo:

P. Ponka, J. Borova, J. Neuwirt and O. Fuchs. *FEBS Lett.* 97:317 (1979).

P. Ponka, J. Borova, J. Neuwirt, O. Fuchs and E. Necas. *Biochim. Biophys. Acta.* 586:278 (1979).

T. Hoy, J. Humphrys, A. Jacobs, A. Williams and P. Ponka. *Br. J. Haematol.* 43:443 (1979).

M. Cikrt, P. Ponka, E. Necas and J. Neuwirt. *Br. J. Haematol.* 45:275 (1980).

C. Hershko, S. Avramovici-Grisaru, G. Link, L. Gelfand and S. Sarel. *J. Lab. Clin. Med.* 98:99 (1981).

D. K. Johnson, M. J. Pippard, T. B. Murphy and N. J. Rose. *J. Pharm. Exp. Ther.* 221: 399 (1982).

A. Williams, T. Hoy, A. Pugh and A. Jacobs. *J. Pharm. Pharmacol.* 34:730 (1982).

S. Avramovici-Grisaru, S. Sarel, G. Link and C. Hershko. *J. Med. Chem.* 26:298 (1983).

E. Baker, M. L. Vitolo and J Webb. *Biochem. Pharmacol.* 34:3011 (1985).

D. R. Richardson, E. Baker, P. Wilairat, M. L. Vitolo and J. Webb in S.

Fucharoen, P. T. Rowley and N. W. Paul (eds.), Thalessemia: *Pathophysiology and Management*, Part B, Birth Defects Foundation, Original Article Series, 23:81 (1988).

P. Ponka, D. R. Richardson, E. Baker, H. M. Schulman and J. Edward. *Biochim. Biophys. Acta.,* 967:122 (1988).

M. L. Vitolo, J. Webb and P. Saltman. *J. Inorg. Biochem.,* 20:255 (1984)

These aforementioned chemical/physical properties of PIH, in our view explain the poor oral efficacy of PIH observed in humans except at doses so high as to have toxic side effects.

Chromatographic investigations have documented instability of PIH under acidic conditions such that dissolution below pH 3 can lead to decomposition of the PIH which is the active chelating species. PIH has been reported to form a 1:1, 1:2 and a 1:5 iron complex. (D. K. Johnson, T. B. Murphy, N. J. Rose, W. H. Goodwin and L. Pickart. *Inorg. Chim. Acta.* 67:159–65 (1982); T. B. Murphy, D. K. Johnson, N. J. Rose, A. Aruffo and V. Schomaker. *Inorg. Chim. Acta.* 66:L67-8 (1982)).

Preclinical investigations in vivo have demonstrated the presence of PIH crystals in the feces of treated animals. This demonstrates that the very limited water solubility of PIH— 0.14 mg/mL (less than one part per 6,000 in water)—can block complete absorption of a solid oral dosage formulation.

SUMMARY OF THE INVENTION

There is provided a novel series of compounds, free of associated water, of the formula

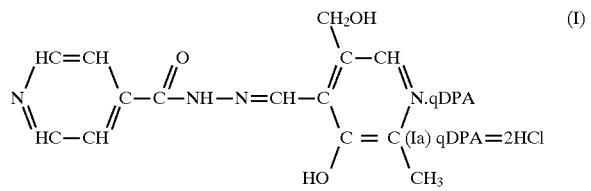

and the E and Z (transoid-anti and cisoid-syn, respectively) isomers thereof, wherein q is 1 or 2, DPA is 2 mols of a monoprotic acid HX, or 1 mol of a diprotic acid $H_2Y$ wherein X is a monovalent anion and Y is a divalent anion and both HX and $H_2Y$ are pharmaceutically acceptable acids sufficiently strong as acids to form I. X is suitably chloride, bromide, iodide, ethanesulfonate, hydrogen succinate or hydrogen sulfate, and $H_2Y$ is suitably dihydrogen sulfate, or 1,2-ethanedisulfonic or any other pharmaceutically acceptable diprotic sulfonic acid. Most suitably X is chloride to yield the anhydrous PIH dihydrochloride (hereinafter abbreviated as PIHDH (Ia) or PIH.2HCl can be used interchangeably).

The compounds of the present invention, in their solid state, are free of associated water. As used herein the term "associated water" is intended to encompass any elements of water revealed by analysis. Such elements comprise, but are not limited to absorbed water, water occluded in the crystal lattice, water of hydration or crystallization or similar mode of association, whether stoichiometric or otherwise.

These polyprotic salts are included in compositions for reducing the level of iron in the cells of living subjects in need of such reduction comprising a reductively effective amount of PIH.DPA (I), suitably PIHDH, and an orally administrable carrier. It is especially desirable to provide these compositions in a dosage form formulated for administration as enterically coated granules, tablets or capsules.

The invention also includes a method of reducing the level of iron in the cells of living subjects in need of such reduction comprising administering to said subject a reductively effective amount of PIH.qDPA, suitably PIHDH. Such methods include administering to said subject a reductively effective amount of these materials in a dosage form formulated for administration as enterically coated granules, tablets or capsules or else in conjunction with sufficient pharmaceutically acceptable buffer to adjust the pH of the stomach of said subject to a level that will minimize acid hydrolysis of the PIH moiety while maintaining a suitable degree of water solubility. Specifically, this requires a pH adjustment of not less than about 3 and not more than approximately a pH of 8.

The ionization curves have been reported for PIH and its complexation products across a broad pH range such that titration curves (D. R. Richardson, L. M. W. Vitolo, G. T. Hefter, P. M. May, B. W. Clare, J. Webb and P. Wilairat. *Inorgan. Chim. Acta.* 170:165–70 (1990); L. M. W. Vitolo, G. T. Hefter, B. W. Clare and J. Webb. *Inorgan. Chim. Acta.* 170:171–176 (1990)) suggest that the protonated species, which would be most soluble for the dihydrochloride prior to conversion to the less water soluble monoprotonated salt, requires a pH no less than approximately 3.

The invention also includes a method of synthesizing the compounds of Formula I which comprises the steps of reacting

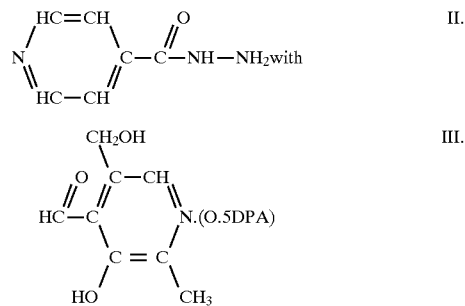

in an anhydrous lower (i.e. C 1–6) alkanol, suitably ethanol, preferably under reflux, to yield

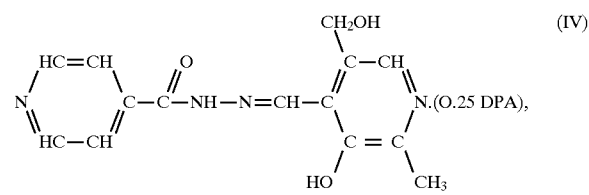

and then reacting the thus produced salt (IV), which is a hemiacid salt where 0.5 DPA is a monoprotic acid with an anhydrous alkali metal hydroxide M.OH, suitably sodium or potassium hydroxide, in the said anhydrous alkanol to yield

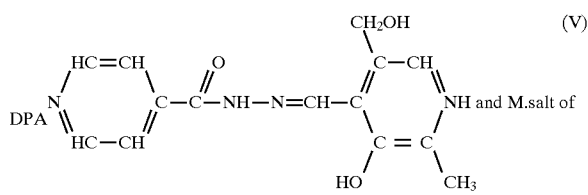

The M. salt is removed and the above anhydrous alkanolic solution of free base (V) treated with at least two equivalents of anhydrous DPA in said anhydrous alkanol to yield the desired polyprotic acid salt (I). Where DPA is a diprotic acid and q in Formula I is 2, then at least four (4) equivalents, i.e., two (2) relative molecules of the acid are needed. As DPA there may be used any strong mono- or diprotic pharmaceutically acceptable acid, whose salts are orally administrable and which is of sufficient strength to diprotonate the PIH molecule. These include: hydrohalic acids, sulfuric acid, phosphoric acid ($H_3PO_4$), trichloro- acetic acid, benzenesulfonic acid, parachlorobenzenesulfonic acid, estolic acid, ethanesulfonic acid, 2-hydroxyethanesulfonic acid, methanesulfonic acid, 2-naphthalenesulfonic acid, p-toluenesulfonic acid and any other sulfonic acid derivatives—mono or diprotic such as 1,2-ethanedisulfonic acid—which are sufficiently acidic to diprotonate the PIH molecule. Dicarboxylic acids such as succinic acid will form, say a dihydrogen-disuccinate.

A variation of this approach is utilized in the synthesis of PIHDH. This method again comprises the previously discussed first steps of reacting II and III.

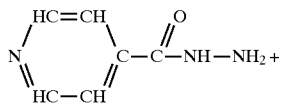

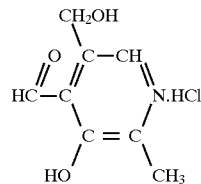

in an anhydrous lower alkanol, again suitably ethanol under reflux, to yield IV as the 0.5 HCl

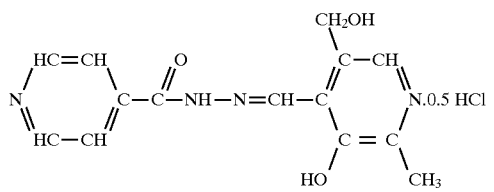

The thus produced hemihydrochloride salt is reacted with at least two equivalents of anhydrous hydrochloric acid in said anhydrous alkanol to yield the desired dihydrochloride salt (IA).

While this method is applicable to other DPA salts, such an approach is not believed to be of practical significance. Pyridoxal is generally commercially available as the monohydrochloride. Thus its conversion to another salt as a mere intermediate is not as advantageous as the approach of forming the free base discussed above.

PIHDH (IA) and certain other PIH.DPA salts free of associated water, have heretofore unreported high levels of water solubility so as to make them pharmaceutically useful compositions of matter for oral administration and absorption into subjects suffering from overload of iron; said PIHDH by virtue of its water solubility provides the iron chelator PIH in a solubilized form which is 450 times more water soluble than PIH itself and which preserves its ability to complex iron in aqueous solutions in vitro and in vivo. These properties of enhanced solubility and complexation together provide the PIH.DPA salts invention with its important pharmaceutical applications, since PIH itself has been reported as not fully absorbed in vivo after oral administration with crystals actually visible in feces of treated subjects. Attempts to use PIH as a clinically useful and reliable drug for iron overload have demonstrated that inadequate levels of iron are removed in humans.

Included in the scope of the invention are the stereoisomeric forms of PIH.DPA believed to exist as the "E" and "Z" isomers shown in (IAi) and (IAii) (S. Avramovici-Grisaru, supra):

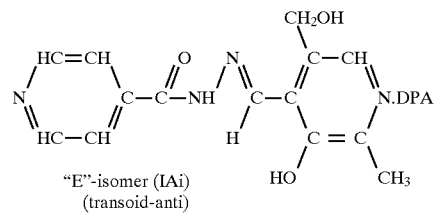

"E"-isomer (IAi)
(transoid-anti)

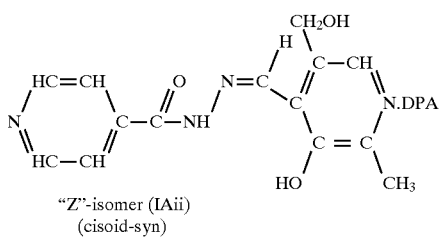

"Z"-isomer (IAii)
(cisoid-syn)

The previously unreported pyridoxal isonicotinyl hydrazone hydrochloride 1.5 hydrate (VI) is prepared by permitting a saturated aqueous solution of PIHDH (IA) to stand at ambient temperature whereby crystals of said monohydrochloride 1.5 hydrate are precipitated.

PIH.DPA especially PIHDH is most suitable for absorption at a pH of 6–7 with virtually little to virtually no decomposition when buffered above 3.0 to 7.0. Such stabilizing of the pH of the environment can be carried out in different ways.

Increasing the pH of the stomach prior to or concurrently with administration of the invention can be accomplished with virtually any pharmaceutically acceptable buffer including, for example a phosphate buffer, a citrate buffer, the pharmaceutically acceptable amino acid glycine, or any combination of buffering agent so as to stabilize the pH of the environment to raise the acidic pH which causes decomposition of the drug. This invention demonstrates that adjustment of stomach pH to 3–4 still allows sufficient concentration of the chelator to be absorbed as to allow for increased iron excretion from patients afflicted with iron overload (Table III).

There may be used a protective coating to delay the dissolution of the active principle until after the drug has passed through the stomach and is introduced into the upper intestinal tract where the pH is sufficiently high to begin dissolution of the protective enteric coating. Once such dissolution begins, the highly water soluble drug rapidly goes into solution in an environment where it tends to be in a form that is both more stable to environmental pH and less highly ionized—which increases the ratio of readily absorbed form of the drug to the highly charged fully protonated form.

The first approach includes the provision of a buffer sachet or packet with sufficient number of milliequivalents of buffer to effectively raise the pH of the stomach. This would normally be 10 to 30 milliequivalents of an appropriate pharmaceutically acceptable antacid which could be any or all of the following, for example: aluminum hydroxide gel, magnesium hydroxide, calcium carbonate, glycine. Other standard antacids could be used as well and could include phosphate-citrate buffers.

A combined buffered tablet could also be given. However, due to the unpleasant taste of the PIH in the mouth, a chewable drug/buffer combination would be unlikely to be well received by users.

DESCRIPTION OF THE PREFERRED EMBODIMENTS

Figure 1:
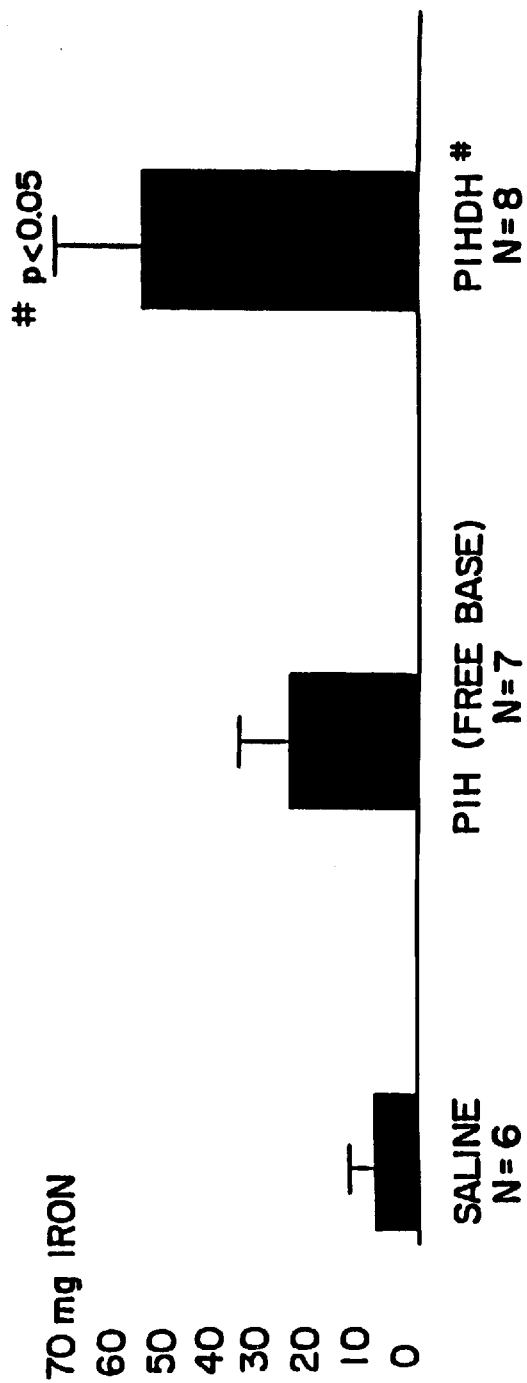
FIG. 1 is a plot of in vivo biliary excretion of iron after oral administration of saline versus iron chelators.
Figure 2:
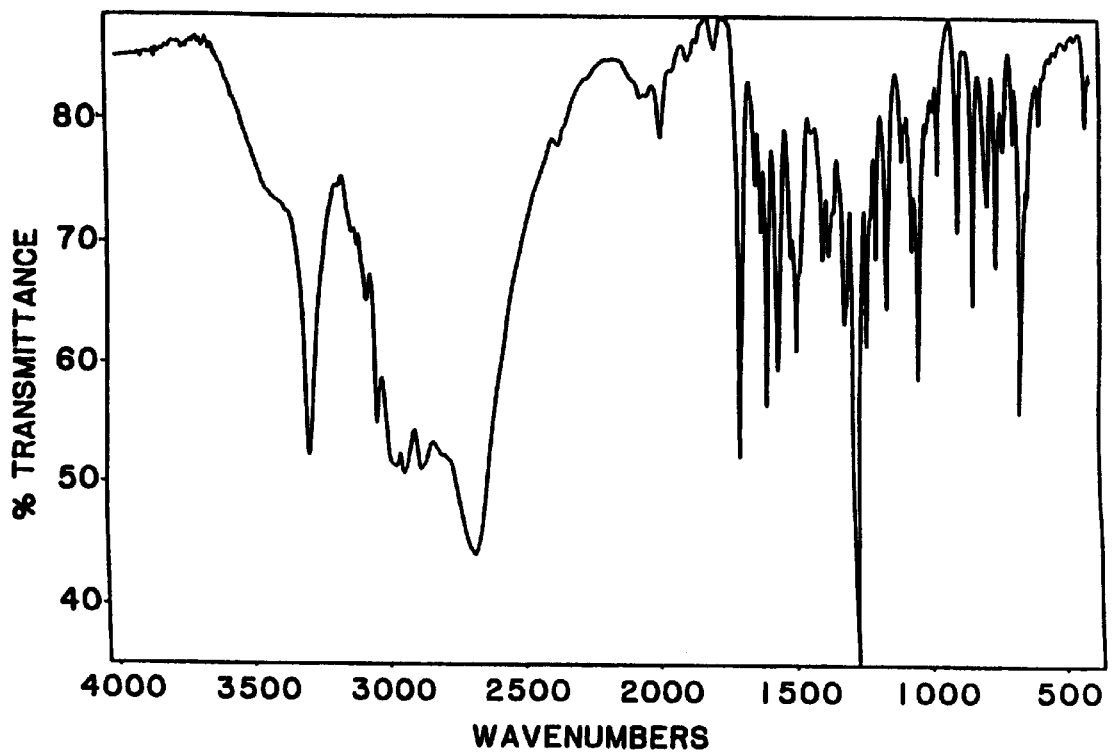
FIG. 2 is an infrared absorption spectrum (KBr, pellet) of PIH dihydrochloride (anh) (i.e. PIH.2HCl).
Figure 3:
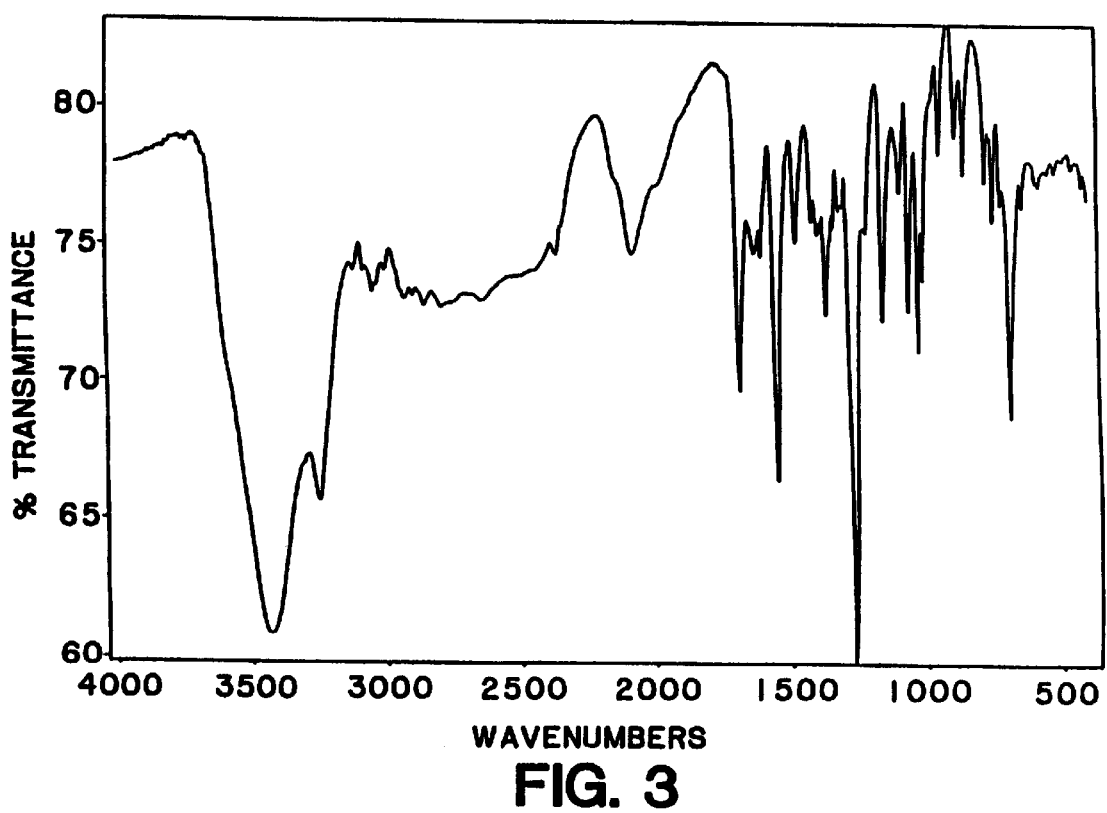
FIG. 3 is an infrared absorption spectrum (KBr, pellet) of PIH monohydrochloride trihemihydrate (i.e. PIH.HCl 1.5 $H_2O$).
Figure 4:
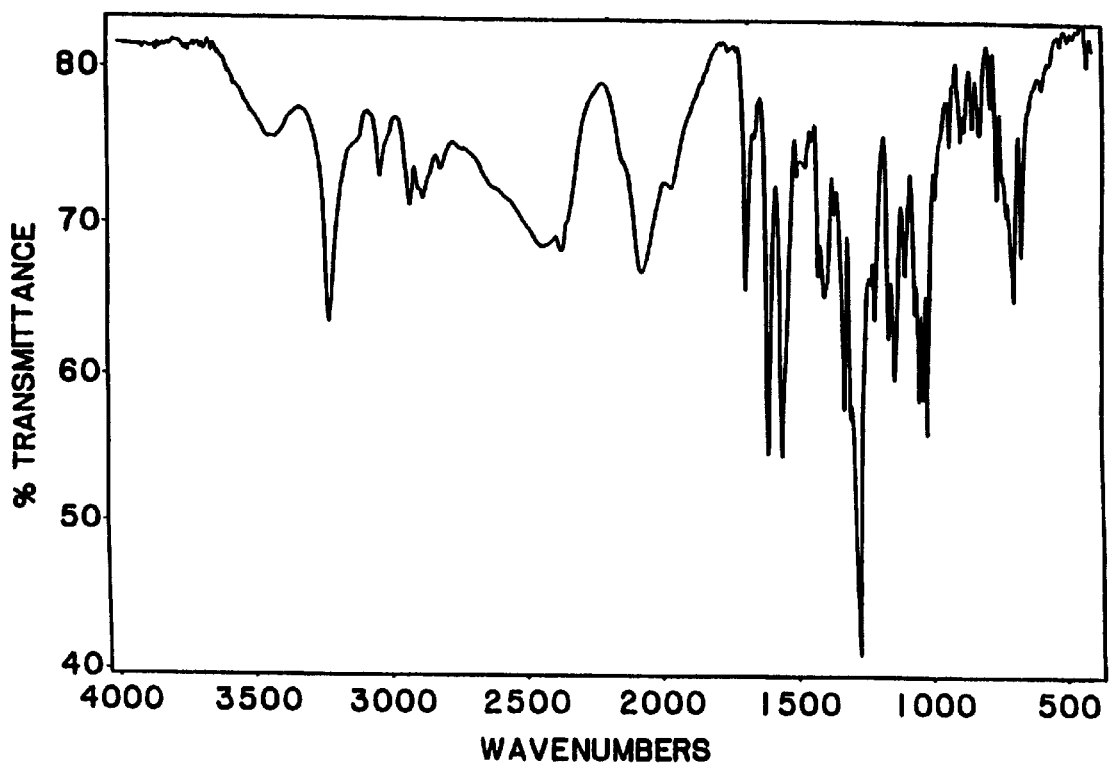
FIG. 4 is an infrared absorption spectrum (KBr, pellet) of PIH hemihydrochloride (anh) (i.e. PIH.0.5 HCl).
Figure 5:
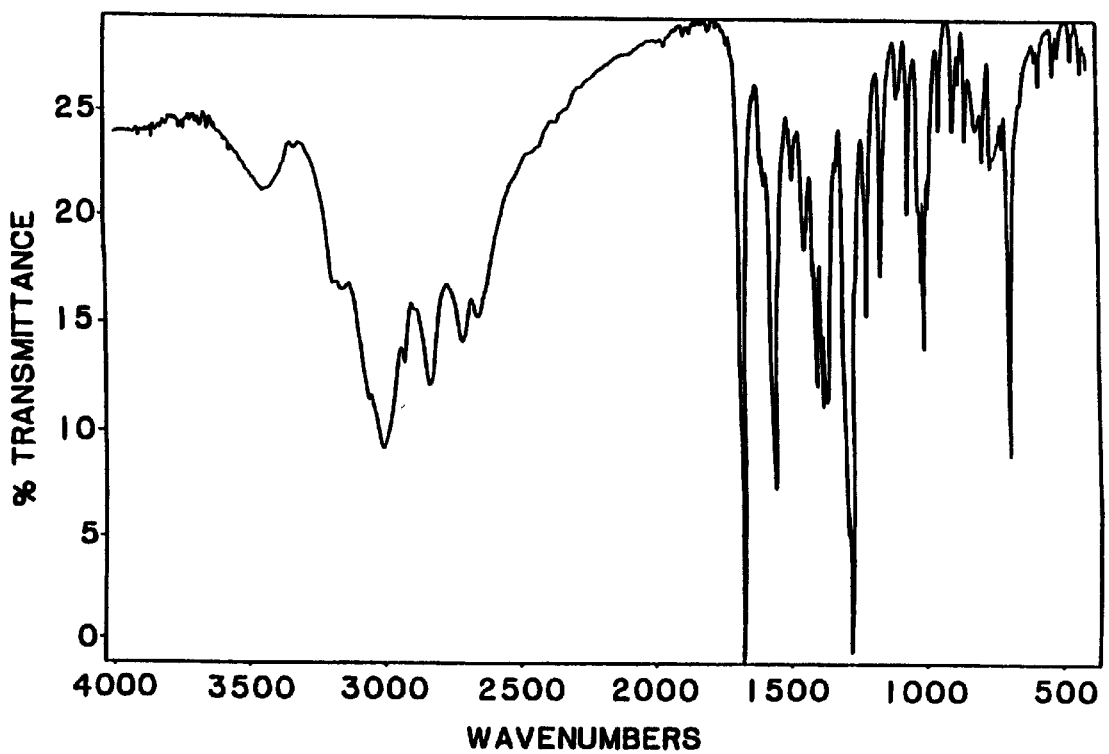
FIG. 5 is an infrared absorption spectrum (KBr, pellet) of PIH free base (anh) (i.e. PIH).
Figure 6:
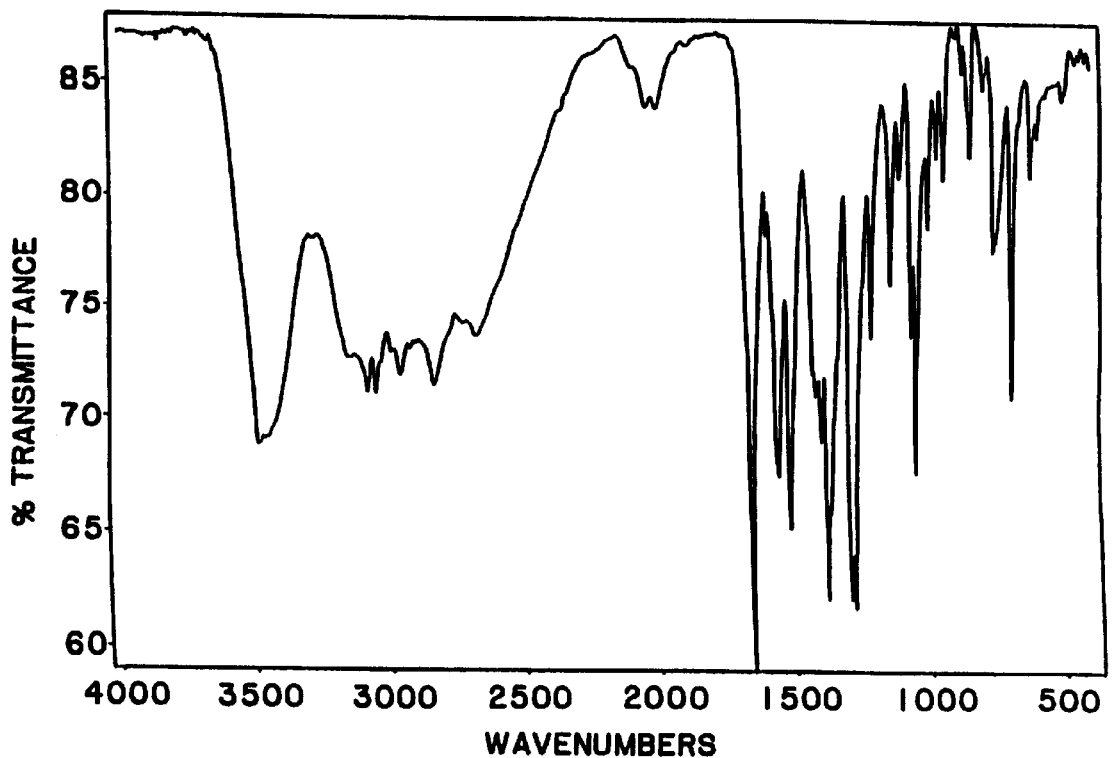
FIG. 6 is an infrared absorption spectrum (KBr, pellet) of PIH free base hydrate (i.e. PIH.$H_2O$).
Figure 7:
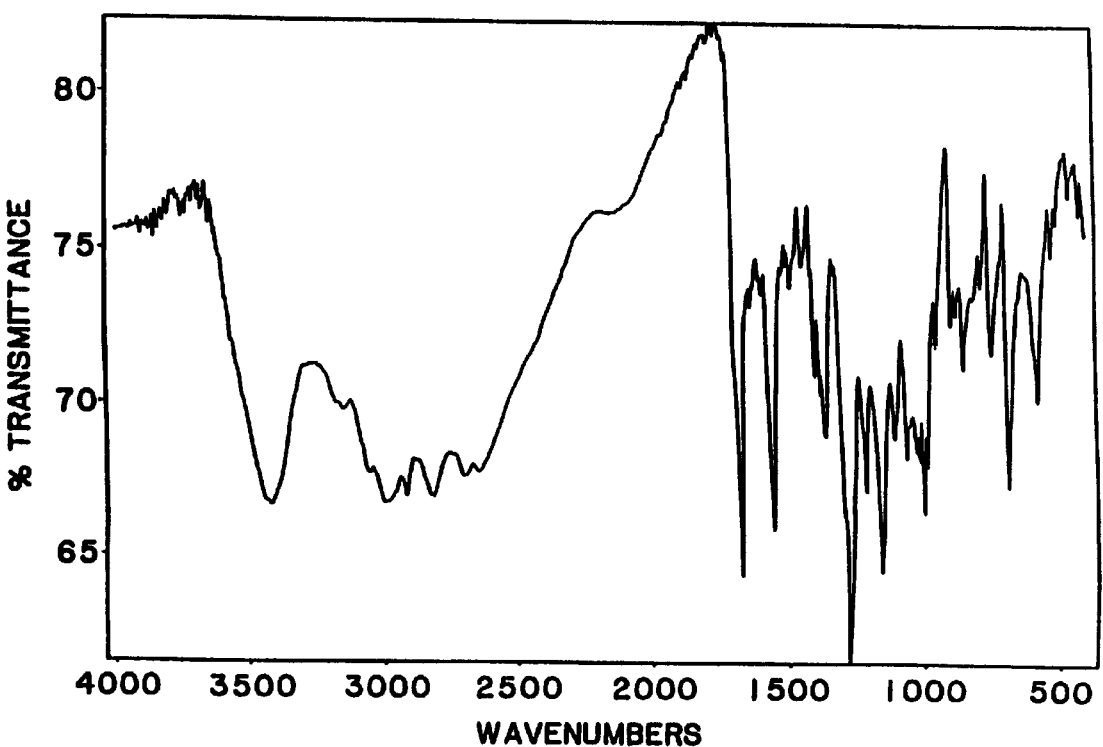
FIG. 7 is an infrared absorption spectrum (KBr, pellet) of PIH hemidihydrogen sulfate) (i.e. PIH. 0.5 $HSO_4H$).
Figure 8:
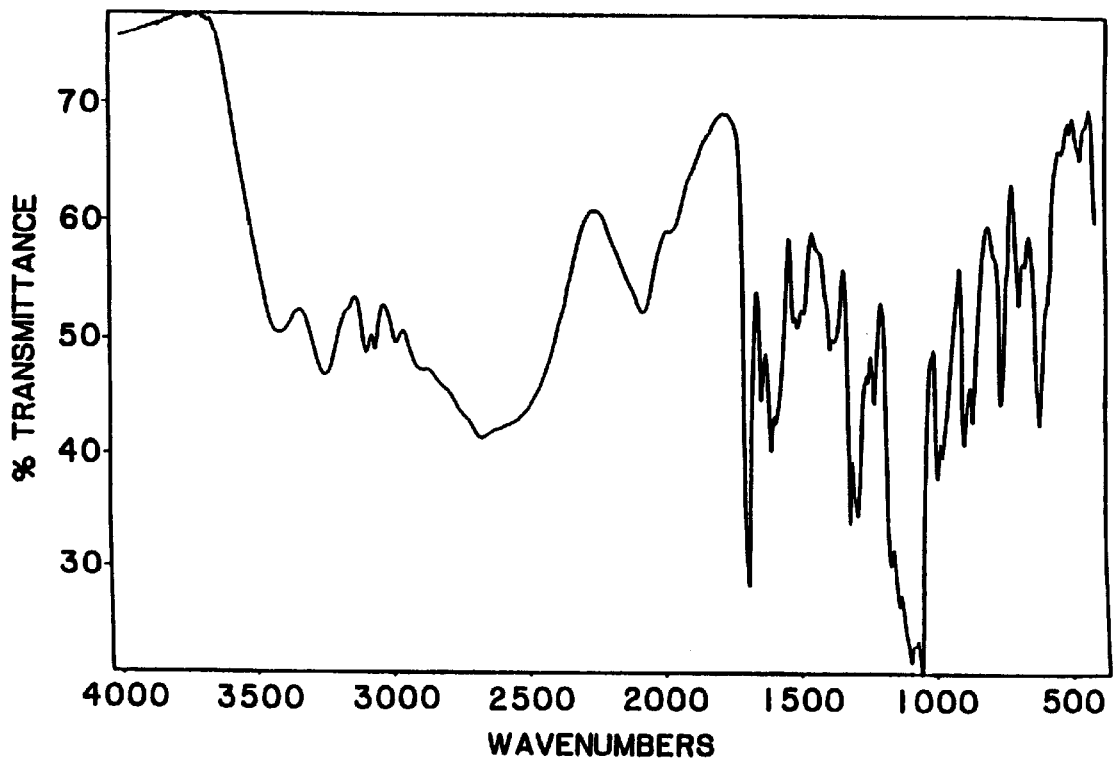
FIG. 8 is an infrared absorption spectrum (KBr, pellet) of PIH di(dihydrogen sulfate) (i.e. PIH. $2HSO_4H$).
Figure 9:
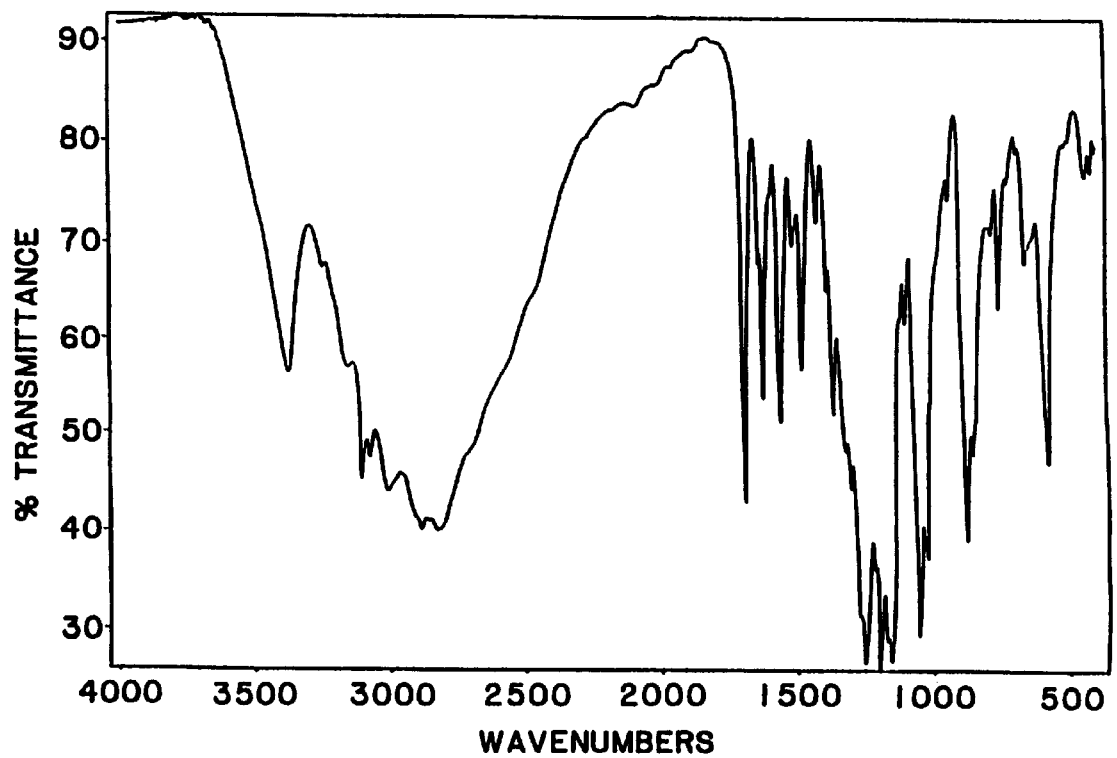
FIG. 9 is an infrared absorption spectrum (KBr, pellet) of PIH dihydrogen sulfate (i.e. PIH. $HSO_4H$).
Figure 10:
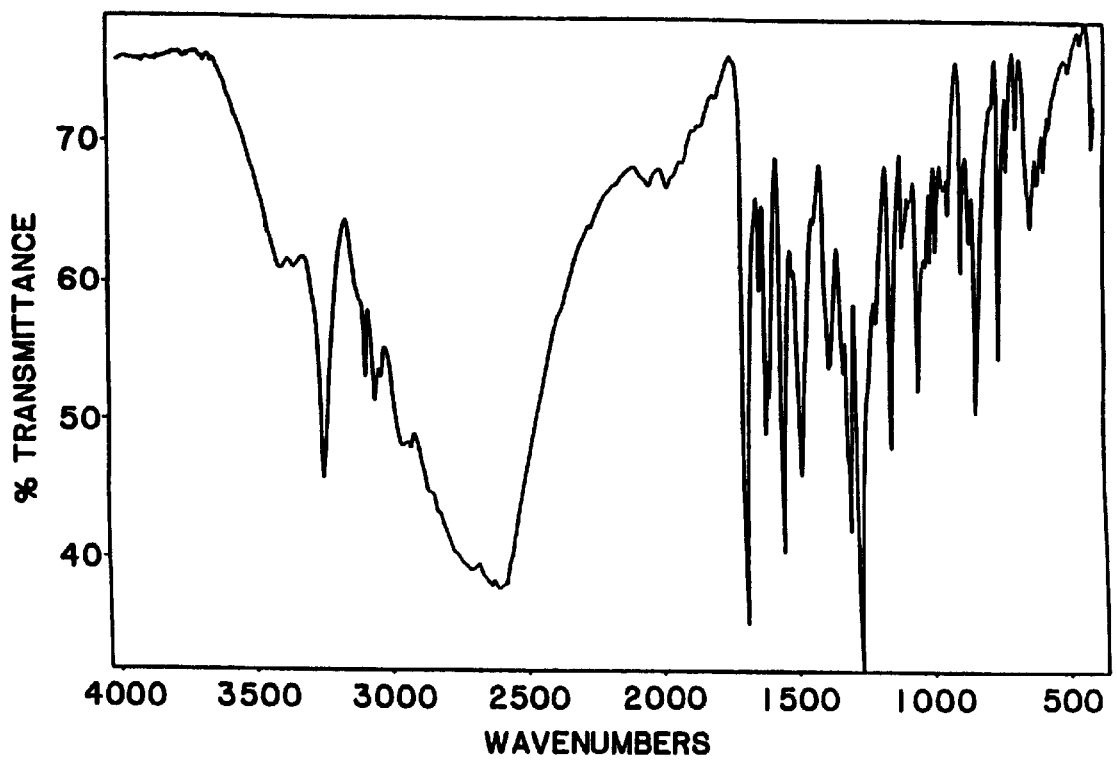
FIG. 10 is an infrared absorption spectrum (KBr, pellet) of PIH dihydro-bromide (i.e. PIH.2HBr).
Figure 11:
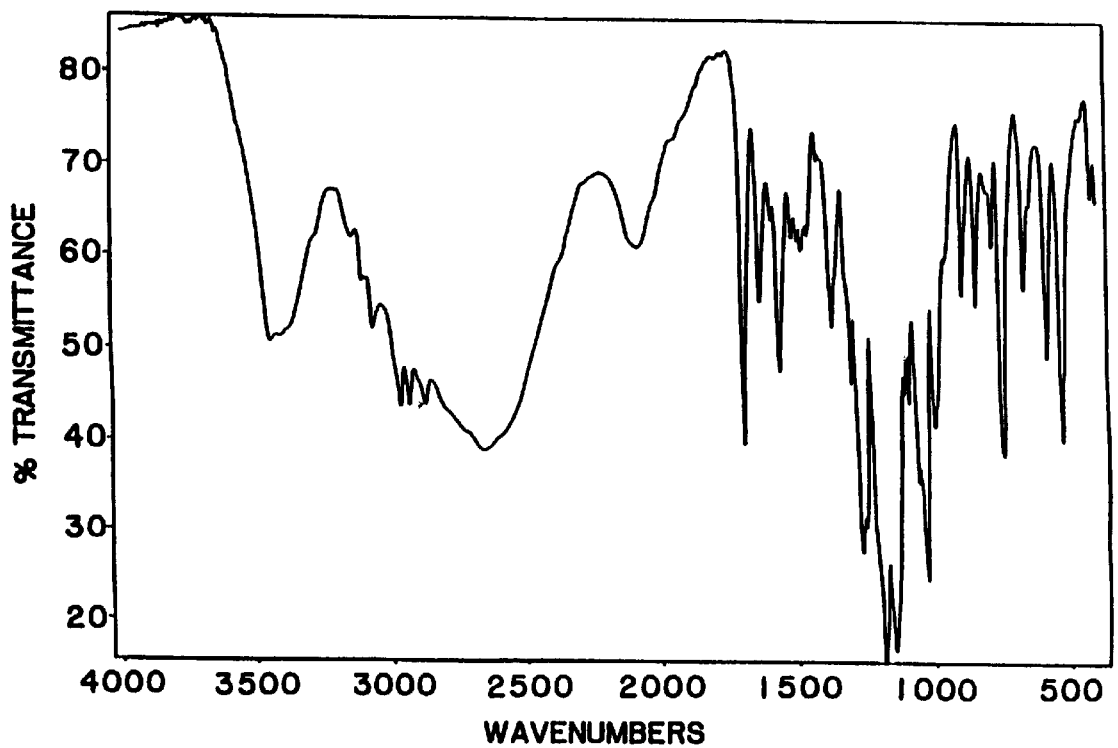
FIG. 11 is an infrared absorption spectrum (KBr, pellet) of PIH di(hydrogenethanesulfonate) (i.e. PIH.$2EtSO_3H$).
Figure 12:
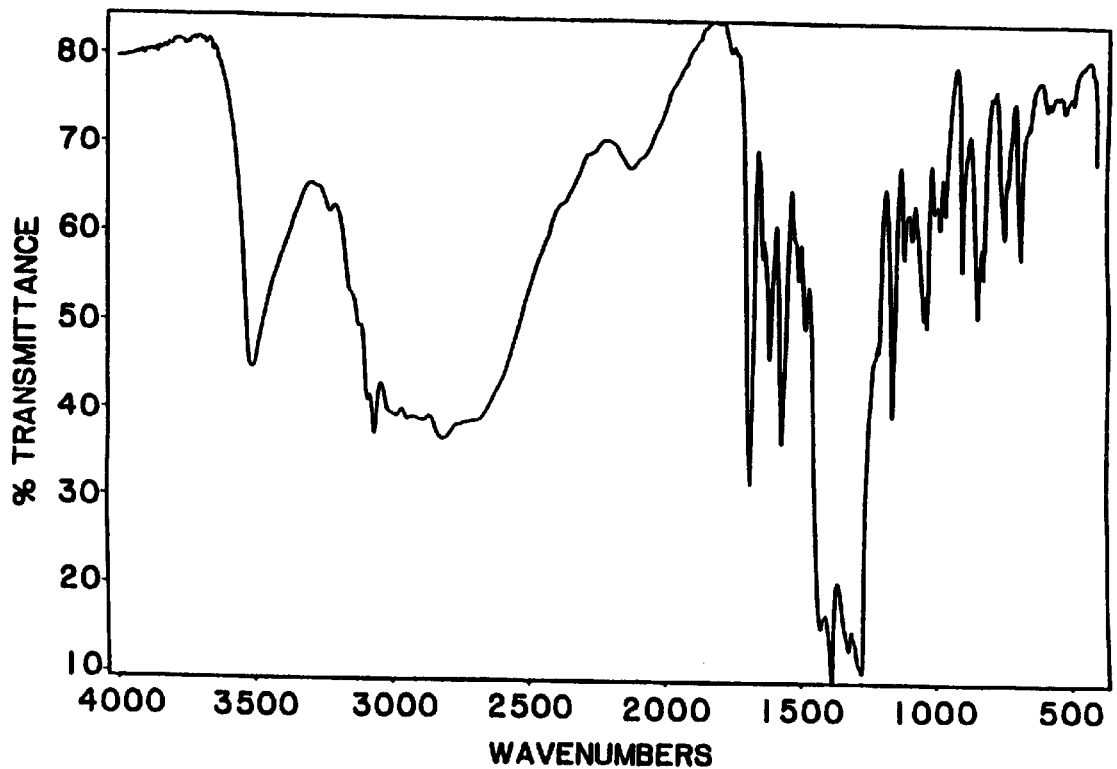
FIG. 12 is an infrared absorption spectrum (KBr, pellet) of PIH di(hydrogen nitrate) (i.e. PIH.$2HNO_3$).
Figure 13:
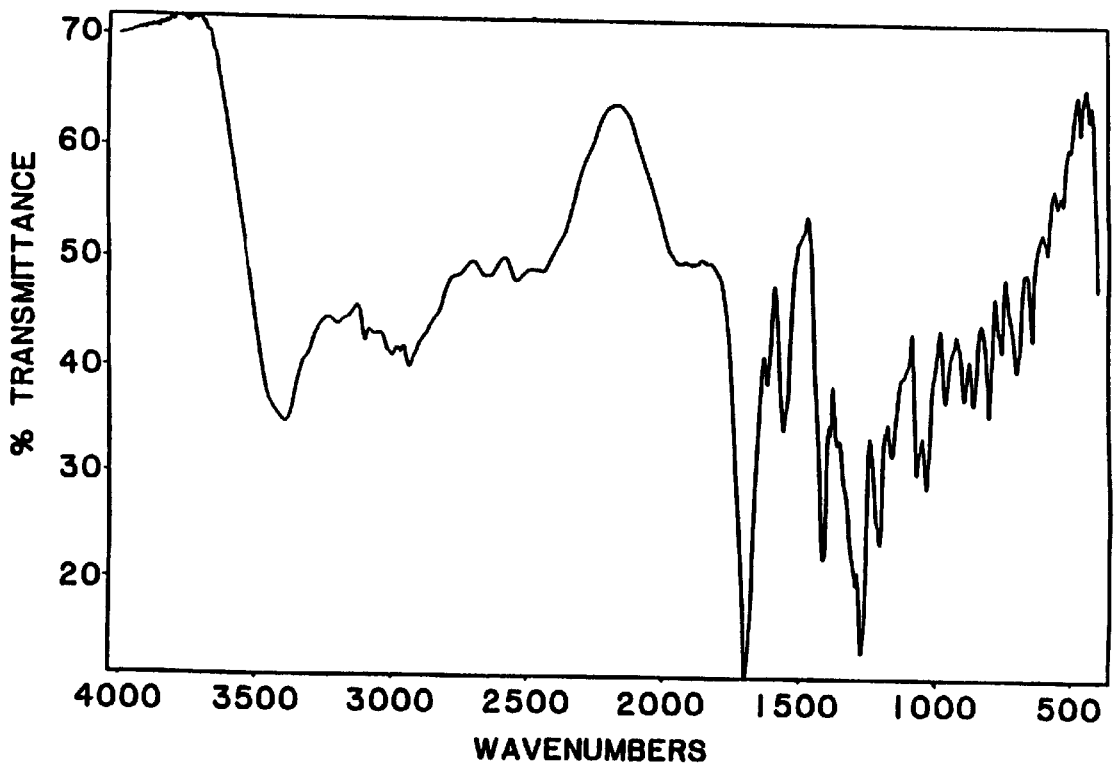
FIG. 13 is an infrared absorption spectrum (KBr, pellet) of PIH dihydrogen disuccinate (i.e. PIH.$2(CH_2CO_2H)_2$).
Figure 14:
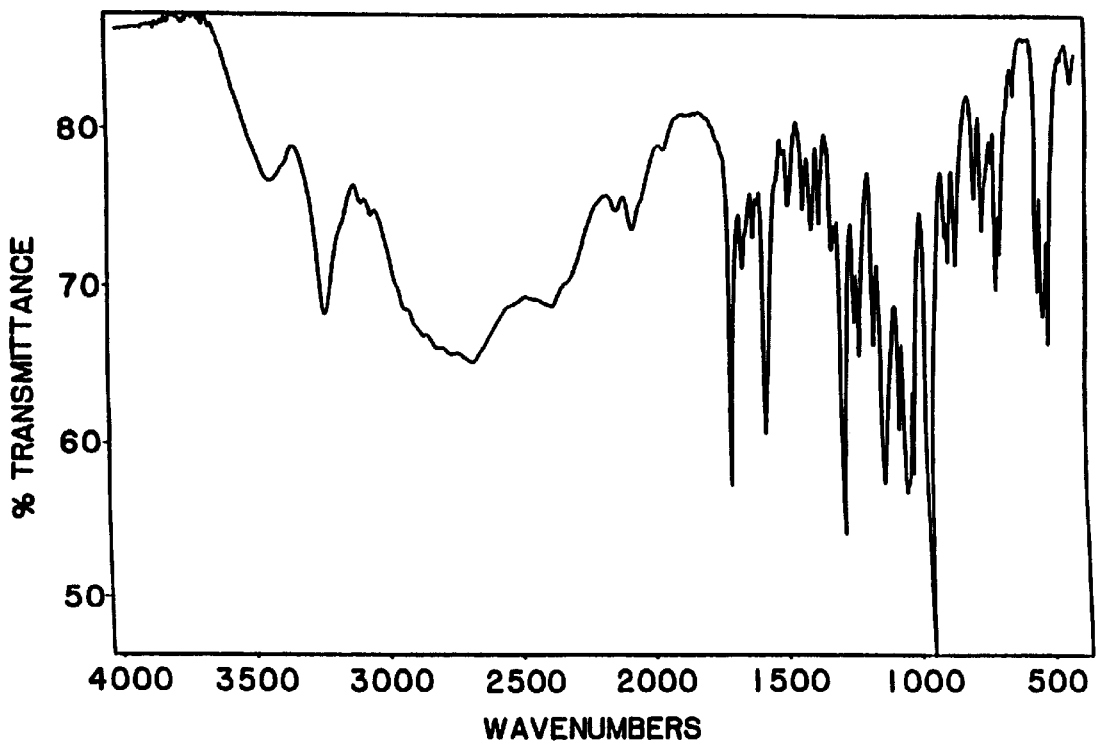
FIG. 14 is an infrared absorption spectrum (KBr, pellet) of PIH trihydrogenphosphate (i.e. PIH.$H_3PO_4$).
Figure 15:
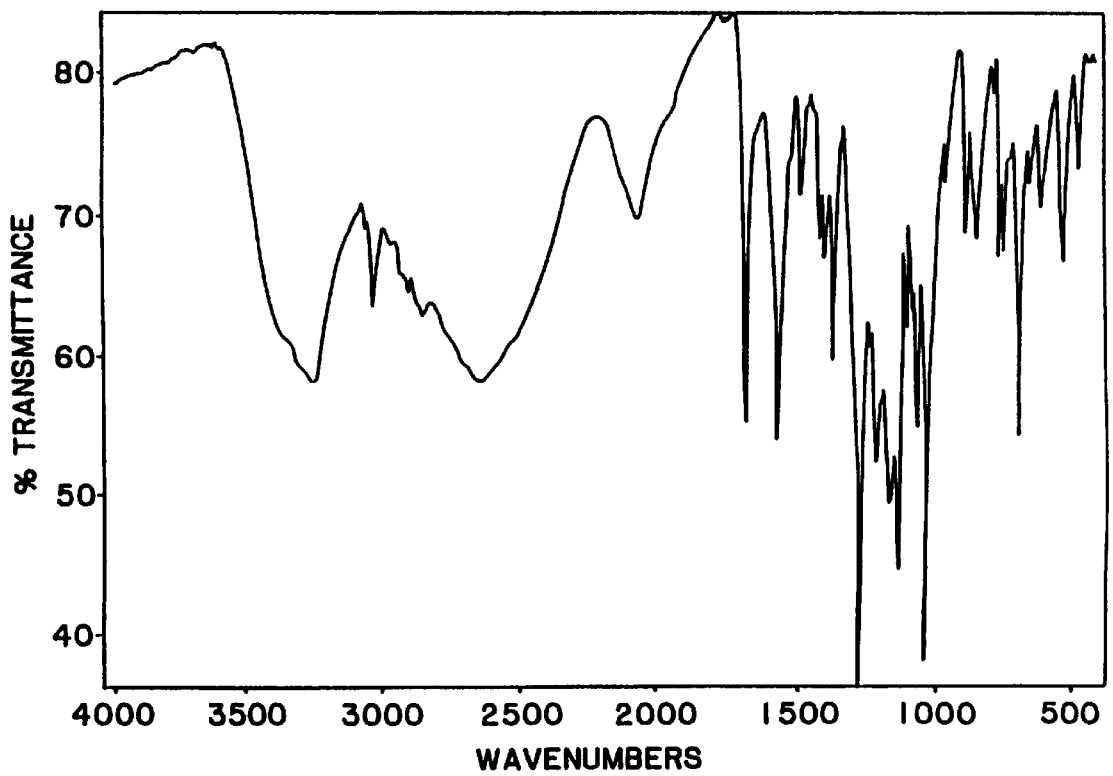
FIG. 15 is an infrared absorption spectrum (KBr, pellet) of PIH isethionate (i.e. PIH.$HO(CH_2)_2SO_3H$).

To a cooled suspension of pyridoxal isonicotinoyl hydrazone 0.25DPA, for example the hemihydrochloride, in absolute ethanol is added slowly with stirring a solution of a slight excess of anhydrous alkali, suitably sodium hydroxide, similarly in anhydrous ethanol. The resultant ethanolic solution of PIH as the anhydrous free base is filtered to remove the thus produced alkali metal salt such as sodium chloride.

To the thus prepared solution of free base are added 2 equivalents of anhydrous DPA such as fuming sulfuric acid, in absolute ethanol, the appropriate PIH.qDPA precipitates from the reaction mixture. In place of sulfuric acid, there may be utilized other acids such as hydrochloric, hydrobromic, hydriodic, ethane sulfonic, trichloracetic or toluene sulfonic acids or similar strong acids capable of forming the corresponding anhydrous diprotic salt. Similarly where, say, the PIH.2DPA is required, such as the PIH.$2H_2SO_4$, 2 equivalents of acid, i.e., sulfuric acid are added.

In a further preferred embodiment, PIHDH is synthesized in high purity in our process in >95% yield in the following manner. Through the use of ultra-filtration and anhydrous specially denatured (SDA) ethyl alcohol as modifications of the previously reported syntheses of PIH from isonicotinic acid hydrazide (11, isoniazid; INH) and pyridoxal hydrochloride (111, 3-hydroxy-5-hydroxymethyl-2- methyl-4-pyridinylcarboxaldehyde hydrochloride), the hemihydrochloride is generated in situ. This is then reacted in situ with a minimum of 2 equivalents of anhydrous hydrogen chloride in anhydrous ethyl alcohol.

$$II + III \xrightarrow[\text{2) excess HCl}]{\text{1) EtOH/ heat}} PIHDH \qquad (IA)$$

Filtration followed by thorough washing with ethanol saturated with hydrogen chloride provides a near quantitative yield of creamy-white crystals which are stable to light and anhydrous heat. After drying, the crystalline PIHDH exhibits superior water solubility at 63 mg/mL as compared to the previously tested PIH base which is soluble at 0.14 mg/mL (>450 times more water soluble).

WATER SOLUBILITY

As shown in FIG. 16, PIHDH demonstrates better water solubility than the free base and its related hydrated species at 25° C. The HCl.1.5 hydrate is isolated as an equilibrium product from concentrated aqueous solutions of PIHDH. Use of a strong inorganic acid such as $H_2SO_4$ in aqueous media can lead to decomposition of the product to pyridoxal hydrazone which can be readily seen, but by substituting a nonprotonic solvent such as ether (THF for example), other pure salts can be isolated.

The immediate water solubility of PIH.qDPAs, when free of associated water, provides unique and highly useful crystalline forms of PIH as polyprotic salts which can become bioavailable rapidly once they are released in the gastro- intestinal tract.

PIH.2HCl is specially prepared in a formulation for oral administration as enteric coated layered granules that protect the PIH.2HCl from extended exposure to stomach acid. The extensive solubility at higher pH makes this formulation suitable for oral use in capsules, coated tablets, or when given directly as a suspension of granules in an appropriate liquid.

Similarly, any other PIH.qDPA salt or derivative thereof, can be formulated to protect the active chelating species from decomposition in stomach acid.

Salts of PIH with pharmaceutically acceptable isethionic $HO(CH_2)_2SO_3H$) acid also show improved solubility over PIH free base.

The slower solubilization of the crystalline monohydrochloride 1.5 hydrate makes this monoacid derivative a less suitable choice for an enterically released material.

ATTEMPTED REPETITION OF SYNTHESES OF U.S. PAT. No. 2,810,725

PIH was first synthesized by Sah supra. S. Archer and M. E. Auerbach, received U.S. Pat. No. 2,775,598 for a method of making PIH via a manganous complex. U.S. Pat. No. 2,810,725 to Bernstein, is the second patent directed to yet another synthesis of PIH. This synthesis is based on the formation of an intermediate stated in this latter patent to be pyridoxal isonicotinoyl hydrazone sulfate (hereinafter PIH.S"). The reaction of PIH.S" with hydrochloric acid and barium hydroxide is stated to yield pyridoxal isonicotinoyl hydrazone (hereinafter PIH"). There is further disclosure of the conversion of PIH" to the corresponding mono- and dihydrochlorides. As summarized above, and reported in detail in the experimental section below, the findings of applicants herein do not support the disclosure of U.S. Pat. No. 2,810,725.

Attempted synthesis of PIH Sulfate (PIH.S")

Applicants attempts to prepare PIH.S" as described in U.S. Pat. No. 2,810,725, failed to give such a compound but gave instead, as would be expected from U.S. Pat. No. 2,775,598, a brown-colored manganese complex of PIH the composition of which was confirmed by manganese analysis as the octahydrate of 2PIH(Mn). This complex is a brown colored material which precipitates rapidly. Since no analysis is given in the patent, it is not clear what the term "sulfate" means.

Independent syntheses of PIH.S" and its salt congeners were carried out. Four different products with unique infrared spectra and physical characteristics are obtained, none of which are orange solids as stated in U.S. Pat. No.2,810,725.

Where concentrated sulfuric acid is used (which is not anhydrous), an off white solid is obtained which analyzed as the diprotic acid addition product containing water of crystallization (0.5 mole of water) (PIH.HSO$_4$H 0.5H$_2$O) with melting point differing by 50 degrees from product PIH.S".

Where fuming sulfuric acid is used (which is anhydrous) in a protic solvent (EtOH), an off white solid is obtained which analyzed as the anhydrous mono-protic acid (one molecule of H$_2$SO$_4$) addition product (PIH.HSO$_4$H) with melting point also differing by 50° from product PIH.S.

Further synthesis in nonprotic solvents provided analytical pure salts of the di(dihydrogen sulfate) (mp 181–183° C.) with 2 mols of H$_2$SO$_4$ (PIH.2HSO$_4$H) and interestingly, an anhydrous hemi(dihydrogen sulfate) (PIH. 0.5(HSO$_4$H), mp 200° C.(d), which is analogous to PIH.0.5HCI).

The heating of PIH sulfuric acid salts always leads to darkening and, not unexpectedly, charring of PIH under the influence of sulfuric acid. This made sharp melting points above 150° C. difficult, if not impossible, to define.

The unusual electronic characteristics of PIH which allow it to selectively chelate iron, can also influence the association of electron rich ions such as HSO$_4$. The analytical data (C, H. N and S are given below) and unique IR's are given below and illustrated in FIGS. 2–14.

By considering the reagents of Example 1 of the U.S. Pat. No. 2,810,725, those knowledgeable in manganese chelation chemistry and having an understanding of the properties of PIH and its derivatives could predict that pyridoxine hydrochloride, manganese dioxide and sulfuamounts should give a amounts should give a pyridoxal hydrochloride plus manganese sulfate and water. The pyridoxal hydrochloride in turn will react with isoniazid to give PIH.HCI which complexes with manganese. As expected, applicants obtained the manganese complex of PIH after the addition of sodium acetate which neutralized any residual mineral acids. These steps are clearly set forth in equations 1 through 3 below, which are consistent with the disclosure of U.S. Pat. No. 2,775,598:

Pyridoxine.HCI+MnO$_2$+H$_2$SO$_4$→$^{(o)}$ Pyridoxal.HCI+ MnSO$_4$+2H$_2$O   (1)   Pyridoxal.HCI+ Isoniazid→PIH.HCI (which chelates Mn$^{++}$)+H$_2$O (2) 2PIH.HCI+MnSO$_4$+4NaOAc→(PIH)$_2$Mn*+2NaCl+ Na$_2$SO$_4$+4HOAc (3)

*2 protons lost in complexing.

It is noteworthy that the process of preparing the manganese complex of PIH, set forth in U.S. 2,775,598 is substantially identical to the procedure stated in Example 1 of U.S. Pat. No. 2,810,725 as yielding the PIH sulfate. Applicants results set forth below confirm those of U.S. 2,775, 598.

Attempted synthesis of PIH

Example 2 of U.S. Pat. No. 2,810,725 discloses that PIH is synthesized from the product obtained above, "prepared as in Example 1" by treatment of a solution of his first product, in a two molar excess of hydrochloric acid, with 1 mole equivalent of barium hydroxide. As discussed above this would be expected to produce the yellow-brown manganese complex of PIH rather than free PIH. This is precisely what applicants found and we were able to confirm again by elemental analysis. Thus, the disclosure of synthesis in U.S. 20 2,810,725 of the PIH sulfate and of PIH by the methods described appears unsupported by experimental fact.

Attempted syntheses of pyridoxal isonicotinoyl hydrazone hydrochloride and dihydrochloride The preparation of PIH mono and dihydrochlorides according to Example 6 of U.S. 2,810,725 were undertaken using equimolar reaction conditions in an effort to duplicate the disclosure of that patents. There was utilized PIH synthesized independently and structurally confirmed beforehand since no reproducible source of PIH was seen to be disclosed in the given in U.S. 2,810,725.

PIH Monohydrochloride:

The PIH hydrochloride preparation disclosed in Example 6 of the patent uses a 1:1 molar ratio of PIH to ethereal HCI. The preparation recites "to a solution of 28.6 grams (0.1M) pyridoxal isonicotinoyl hydrazone in 500 cc absolute ethanol is added 25 cc 4 N (0.1 M) ethereal HCI. After the addition of 500 cc dry ether, the hydrochloride precipitates out. It is filtered off and recrystallized from a mixture of absolute ethanol and ether."

PIH has very limited solubility in water and ethanol, and in fact, to solubilize 28.6 grams of PIH would require 30,000 cc of absolute ethanol. Nevertheless, the aforesaid molar concentrations were used to produce a suspension to which was added the ethereal HCI solution. The "product" was filtered and an attempt was made to recrystallize it according to the disclosure—which required the volume of 2.5 liters of ethanol per 1 gram of recovered solid (a ratio of 2000:1 !!!).The product thus obtained failed to analyze for PIH monohydrochloride or any of its hydrates or solvates.

PIH Dihydrochloride

In a preparation similar to the above relating to PIH monohydrochloride, U.S. 2,810,725 provides in Example 6, for the use of a 2:1 molar ratio of ethereal HCI to PIH and again recites "to a solution of 28.6 grams (0.1 M) pyridoxal iso-nicotinoyl hydrazone in 500 cc absolute ethanol is added 50 cc 4 N (0.2M) ethereal HCI. After the addition of 500 cc dry ether, the hydrochloride precipitates out. It is filtered off and recrystallized from a mixture of acetonitrile and ether."

As a result of applicant's work, this procedure raises even more questions of operability than the immediately preceding one, since the acetonitrile solubility of the precipitate obtained after treatment of an authentic sample of PIH with ethereal HCI, is virtually nil. Specifically, attempts to solubilize the product succeeded in dissolving only 40 ma of material per 500 cc of hot acetonitrile—a ratio of 1 gram per 12.5 liters of acetonitrile (a ratio of 10,000:1) and no precipitate was obtained after addition of dry ether—even upon cooling the solution. Applicants were unable to liberate any product from the recrystallization system disclosed in U.S. 2,810,725.

CONCLUSIONS

It is clear from the experimental results reported herein that the synthesis and isolation of pyridoxal isonicotinoyl hydrazone (PIH), and its derivatives, that the products and methodology disclosed in U.S. Pat. No. 2,810,725 cannot be replicated. The key compound claimed is pyridoxal isonicotinoyl hydrazone sulfate (Example 1), but the product obtained from Example 1 synthesis is not the PIH sulfate. The product is a manganese complex of PIH, which confirms the disclosure of an earlier patent, U.S. Pat. No. 2,775,598. Furthermore, this erroneously identified product is incapable of forming the parent molecule pyridoxal isonicotinoyl hydrazone as recited in Example 2 of U.S. Pat. No. 2,810,725.

Within Example 6 of U.S. Pat. No. 2,810,725, the syntheses of other pyridoxal isonicotinoyl hydrazone acid-addition salts are recited but it is apparent that the methodology, as described—even when utilizing PIH synthesized by a provable route and the structure of said PIH confirmed prior to derivatization—do not substantiate any of the known solubility properties of PIH or more specifically, its polyacid addition salts. The recitations, in Example 6, concerning the recrystallization of the mono and dihydrochloride salts of PIH, do not support the structures allocated to them.

EXAMPLE OF BIOLOGICAL ACTIVITY OF THE INVENTION

Experiments by several investigators have shown that in rats, PIH when administered as a continuous infusion in solution, produces quantitatively similar iron excretion as compared to an effective injectable iron chelator, desferrioxamine. There has, heretofore been no convenient, safe and effective orally administered chelator that has been developed for clinical use. In phase I clinical trials in humans, PIH proved to be highly unpalatable with a lingering unpleasant taste and oral sensation that makes compliant adult use of a soluble liquid formulation questionable and pediatric use doubtful. When PIH was administered orally in capsule form to people, the required doses (>60 mg/kg) needed to elicit sufficient iron excretion, were accompanied by toxicity characterized by elevated hepatic enzymes.

Preliminary human studies demonstrate that the iron excretion of the oral form of PIH, given at three times the molar rates, without improved stability and solubility, was less than half of that expected with subcutaneously injected desferrioxamine.

The purpose of the present invention was to enhance the immediate water solubility of the active principle and thus develop an effective and efficient way to deliver the pharmacologically active chelating species, which has excellent partition in lipids. The enhanced solubility thus encourages absorption from the gastrointestinal tract and the proper enteric formulation carries the active principle through the stomach where it eliminates exposure to aqueous acid which can decompose PIH and PIHDH. Some decomposition has been observed for PIHDH in strongly acidic medium but the PIHDH is more stable with no degradation at pH 6.8, 17.7% at pH 2.78 and 44.1% at pH 1.29 after three hours.

The superior in vivo efficacy of the highly water soluble PIHDH can be seen in FIG. 1 and the table in FIG. 17. This demonstrates that the PIHDH, as gavage at 100 mg/kg led to a total biliary Iron excretion 2.5 times greater (250%) than the less water soluble PIH at an equivalent dosage when administered to iron-overloaded rats.

METHODOLOGY FOR BIOASSAY

Measurement of the bioefficiency of iron chelators have been carried out in rats using the methods of Brittenham supra and Park et al,(C. Park, B. R. Bacon, G. M. Brittenham and N. Tas. Lab Invest. 57:555–63 (1987).

Male Sprague-Dawley rats weighing approximately 200 g were housed in cages and randomly assigned to three groups containing at least 6 animals. The groups received (i) one ml of saline alone administered by gavage (ii) 1 mL saline with PIH as the free base, 100 mg/kg body weight, added just prior to administration by gavage and (iii) 1 mL saline with PIHDH, 100 mg/kg body weight, added just prior to administration by gavage. The doses of chelators tested are chosen to provide direct comparisons with previous assay data. Animals receiving the chelators or saline by gavage receive doses 45 minutes prior to surgery. Animals are placed under anesthesia and the bile duct cannulated to permit continuous collection of bile during the assay time period. The bile is collected at half-hour intervals for 5 or 6 hours and the iron content determined spectrophotometrically, using bathophen-anthroline sulfonate for color development as published by Pippard et al, (M. J. Pippard, D. K. Johnson and C. A. Finch. Blood. 58:685–92 (1981)).

To detect differences between the experimental groups in the mean values of biliary iron excretion, analysis of variance procedures will be used with drug treatment as the grouping factor. A significance level of 0.05 is selected as a standard measure of efficacy.

MODE OF ADMINISTRATION

The active compounds of this invention are administered orally in such a manner that degradation in the stomach is avoided or substantially reduced. This may be done by administration as enterically coated dosage forms such as granules, tablets or capsules. Alternatively, where such coating is not used, the compounds are administered either together with or after preadministration of a buffer to increase the pH of the stomach into the range of above 3 to about 7.5, suitably about 4 to 7. Such buffers are well known to include single or multiple components such as those listed in the US Pharmacopoeia XXII, specifically for example, ammonium, potassium and/or sodium salts of phosphoric acid, in con-junction with citric acid. Use of a pharmaceutically acceptable antacid, such as aluminum and/or magnesium hydroxide or calcium carbonate or glycine USP/NF sufficient to neutralize the normally present 0.1 N HCI in the 200 to 600 ml of stomach fluids (20 to 60 meq of base). A specific example of phosphate-citrate buffer, pH 6.8, would result from 9.1 ml of 0.1 M citric acid combined with 40.9 ml 0.2M dibasic sodium phosphate solutions. A further example is prior adminis-tration of 3.0 grams of glycine (Aminoacetic acid) USP/NF which demonstrably raises the pH of the stomach contents with 100 mL of water to pH 3.0 to 4.0 as measured by a clinically accepted pH indicator string test (for example, Gastro-test device for rapid measurement of gastric pH and screening for esophageal and gastric bleeding, U.S. Pat. Nos. 3,683,890–3,528,429, HDC Corp., San Jose, Calif. 95131).

Clinical Results

The clinical utility of two formulations of PIHDH are presented in Table III. Table III shows the total daily iron excretion, measured in mg/day, in iron overloaded patients after a resting period. Five human subjects were administered PIHDH (PIH(HCl)$_2$) as either enteric coated granules at 546 mg three times daily representing the lowest dose tested at 20 mg/kg per day. In addition, three subjects were also given 546 mg capsules of the same active chelating drug, three times daily, for six days immediately after administration of 3.0 grams of glycine USP/NF to bring the stomach pH approximately to 3–4 as measured by gastric string pH test. All tests were performed on patients kept in hospital and excreta were collected with total iron excretion determined by laboratory extraction methods comparable to those reported for other in vivo testing using the methods of Brittenham supra, Park et al. supra, and Pippard supra.

These data in FIG. 18 demonstrate that either enteric granules, protecting PIHDH from stomach acid, or buffered capsules, are both adequately absorbed to allow for increased excretion of iron from 139% to 288% of the baseline iron excretion of patients with iron overload.

PIH.qDPA suitably as the PIHDH is utilized to deliver the equivalent of 250–1500 mg of chelator up to three times daily depending upon the speed of absorption of the drug and the severity of the clinical symptoms requiring chelation therapy. This is also controlled by enteric coating which can slow dissolution and provide a delayed release formulation. The target dosage is 15–60 mg/kg total per day of active chelator which can complex sufficient iron or other target ions so as to be pharmaceutically effective.

EXAMPLE 1

Pyridoxal isonicotinoyl hydrazone dihydrochloride: PIHDH;3-hydroxy-5-( hydroxy- methyl)-2-methyl-4-pyridinecarboxaldehyde-4' pyridinecarboxylic acid hydrazone dihydrochloride(l)

A chemical reactor system, fitted with an efficient reflux condenser and efficient mechanical stirrer, is charged with 27.2 kg of anhydrous ethyl alcohol and 1000 g. (7.30 Mol) of isoniazid (II) and the solids fully dissolved by gradual heating and stirring. Pyridoxal Hydrochloride (III; 1651 g., 7.76 Mol) is then added with stirring and the mixture refluxed for one hour during which time the highly insoluble orange colored crystalline PIH-0.5HCl is formed. Stirring is continued for one hour and 1900 mL of anhydrous ethyl alcohol saturated with 830 g. of HCl gas is added to the mixture. Stirring is continued for 14 hours at which time the viscous cream-colored suspension is filtered and washed with ethanol saturated with HCl gas. The solid is dried under vacuum to yield 2542 g. (97.0%) of dry pyridoxal isonicotinoyl hydrazone dihydrochloride as an off-white solid, with melting point 255°–260° C. (decomposition).

I.R. (KBr Pellet): 3288, 2676(vbr), 1697, 1598, 1556, 1488, 1311, 1269, 1228, 1036, 836, 657 cm$^{-1}$ Calculated for $C_{14}H_{14}N_4O_3 \cdot 2HCl$ C: 46.81 H: 4.49 N: 15.60 Found: C: 46.87 H: 4.56 N: 15.60

EXAMPLE 2

Pyridoxal isonicotinoyl hydrazone hydrochloride 1.5 H$_2$O; PIHHCl.1.5 H$_2$O;3-hydroxy-5-(hydroxymethyl) -2-methyl-4-pyridinecarboxaldehyde -4' pyridin ecar-boxylic acid hydrazone monohydrochloride trihemihydrate A saturated water solution of PIHDH (63 mg/mL) when allowed to stand undisturbed for one hour forms white crystals of the heretofore unreported hydrochloride-1.5 hydrate of PIH which retains water solubility of 34 mg/mL, mp 253° C. (decomposition).

I.R. (KBr Pellet): 3432, 3251, 2079, 1687, 1550, 1368, 1268, 1156, 1062, 1026, 1009, 691 cm$^{-1}$ Calculated for $C_{14}H_{14}N_4O_3 \cdot HCl \cdot (1.5H_2O)$ C: 48.07 H: 4.98 N: 15.88 Cl: 10.06 Found: C: 48.07 H: 5.19 N: 16.02 Cl: 10.14

EXAMPLE 3

Pyridoxal isonicotinoyl hydrazone free base (as an anhydrous intermediate for diprotic salts)

To a cooled suspension of pyridoxal isonicotinoyl hydrazone 0.5 hydrochloride (254 g., 0.72 Mol) formed in Example 1. in 2.7 liter of water is added slowly with stirring a solution of 14.4 g (0.36 Mol, 1 equivalent) anhydrous sodium hydroxide in 150 mL water. The resultant suspension of PIH hydrate is filtered, dried and dissolved in 9 liters of hot anhydrous methanol. The solution is allowed to cool thus precipitating the anhydrous pyridoxal isonicotinoyl hydrazone as the free base (160 g., 77.7% first crop).

EXAMPLE 4

Pyridoxal isonicotinoyl hydrazone di(hydrogenethanesulfonate) (PIH.2EtSO$_3$H)

To the free base prepared in Example 3 were added 2 equivalents of anhydrous ethane sulfonic acid in absolute ethanol. The title product precipitated from the reaction mixture as off white crystals m.p. 182°–4° C. (dec).

I.R. (KBr Pellet): 3446, 2661 (vbr), 2070, 1698, 1563, 1303, 1272, 1255, 1187,1149,1032,996,751, 743,582, 530 cm$^{-1}$ Calculated for $C_{14}H_{14}N_4O_3 \cdot 2 EtSO_3H$ C: 42.67 H: 5.17 N: 11.06 Found: C: 42.53 H: 5.08 N: 11.33

In accordance with the above procedure, but where in place of ethane sulfonic acid, there is utilized hydrobromic, hydriodic, nitric, succinic, trichloracetic, toluene sulfonic or fuming sulfuric acid, there are obtained the corresponding anhydrous polyprotic salts.

Pyridoxal isonicotinoyl hydrazone dihydrobromide (PIH.2HBr)

I.R. (KBr Pellet): 3244, 2602 (vbr), 1685, 1611, 1598, 1546, 1480, 1302, 1269, 1152, 1060, 836, 751 cm$^{-1}$ Calculated for $C_{14}H_{14}N_4O_3 \cdot 2 HBr$, m.p. 230°–232° C. C: 37.52 H: 3.60 N: 12.50 Found: C: 37.34 H: 3.61 N: 12.45

Pyridoxal isonicotinoyl hydrazone dihydrogen disuccinate {PIH.2(CH$_2$COOH)$_2$}

I.R. (KBr Pellet): 3393, 2933 (vbr), 1694, 1557, 1414, 1298, 1272, 1204, 1156,1070,1028,958, 890, 858,800, 699 cm$^{-1}$ Calculated for $C_{14}H_{14}N_4O_3 \cdot 2 CH_2COOH)_2$, m.p. 168°–170° C. C: 50.57 H: 5.00 N: 10.72 Found: C: 49.96 H: 4.74 N: 10.51

Pyridoxal isonicotinoyl hydrazone di(hydrogen nitrate) {PIH.2(HNO$_3$}

I.R. (KBr Pellet): 3508, 3060, 2811 (vbr), 1682, 1612, 1565, 1424, 1385, 1322, 1277, 1156, 1045, 1031, 900, 845, 823, 742, 683 cm$^{-1}$ Calculated for $C_{14}H_{14}N_4O_3 \cdot 2HNO_3$, m.p. 155° (d) C: 40.78 H: 3.88 N: 20.37 Found: C: 40.83 H: 3.81 N: 20.28

EXAMPLE 5

Pyridoxal isonicotinoyl hydrazone dihydrogen sulfate (PIH.HSO$_4$H)

To the free base prepared in Example 3 was added 1 mole of fuming sulfuric acid in anhydrous ethanol. The title product precipitated from the reaction mixture as off white crystals m.p. 200°–205° C. (dec).

I.R. (KBr Pellet): 3236, 3088, 2660, 2069, 1685, 1638, 1598,1579, 1307, 1282, 1158, 1136, 1093, 1055, 985, 966, 882, 852, 746, 607 Cm$^{31}$ $^1$ Calculated for $C_{14}H_{14}N_4O_3 \cdot H_2SO_4$. C: 43.74 H: 4.19 N: 14.57 S: 8.32 Found: C: 44.11 H: 4.46 N: 14.26 S: 8.26

EXAMPLE 6

Pyridoxal isonicotinoyl hydrazone di(dihydrogen sulfate) (PIH.2HSO$_4$H)

To the free base prepared in Example 3 were added 2 moles of fuming sulfuric acid in tetrahydrofuran. The title product precipitated from the reaction mixture as off white crystals m.p. 181°–183° C.

I.R. (KBr Pellet): 3372, 3106, 3006, 2825, 1662, 1623, 1559, 1479, 1257, 1204, 1176, 1160, 1058, 1027, 880, 857, 581 cm$^{-1}$ Calculated for $C_{14}H_{14}N_4O_3 \cdot 2H_2SO_4$. C: 34.85 H:3.76 N: 11.61 S: 13.29 Found: C: 34.69 H: 3.33 N: 11.17 S: 13.06

EXAMPLE 7

Pyridoxal isonicotinoyl hydrazone hemidihydrogen sulfate) (PIH.0.5HSO$_4$H)

To the free base prepared in Example 3 was added 1 mole of fuming sulfuric acid in tetrahydrofuran. The title product precipitated from the reaction mixture as off white crystals m.p. 200°–205° C. (dec).

I.R. (KBr Pellet): 3442, 3423. 3002, 2823, 2705, 2648, 1675, 1559, 25 1362, 1278,1215,1162,1003, 851,742, 690, 578cm$^{-1}$ Calculated for $C_{,14}H_{14}N_4O_3 \cdot 0.5H_2SO_4$. C: 50.15 H: 4.50 N: 16.70 S: 4.77 Found: C: 49.66 H: 4.53 N: 16.46 S: 4.69

EXAMPLE 8

Pyridoxal isonicotinoyl hydrazone isethionate)(PIH.HO (CH$_2$)$_2$SO$_3$H)

To the free base prepared in Example 3 were added (340 mg,1.2mM) was added 1.0 ml of a 1.2 molar solution of isethionic acid (1.2 mMol)in ethanol and 20mi of methanol. The mixture was heated to boiling wherein all solids were soluble. The solution was allowed to cool to 25° C. and the resultant precipitate filtered off, washed with ethanol (1×3 ml) and the orange solid vacuum dried to give 420mg (100%) of the title product with water solubility of 2.7ml/mg and solubility in 0.1NHCI-36mg/ml, mp 203°–205° C. 2 equivalents of anhydrous ethane sulfonic acid in absolute ethanol. The title product precipitated from the reaction mixture as off white crystals m.p. 203°–5° C. (dec).

I.R. (KBr Pellet): 3275, 3057, 2873, 2660(br), 2068, 1677, 1581, 1366, 1275, 1168, 1033, 883, 757, 689cm, Calculated for $C_{14}H_{14}N_4O_3 \cdot C_2H_6SO_4$ C: 46.59 H: 4.89 N: 13.59 S: 7.77 Found: C: 46.83 H: 4.82 N: 13.59 S: 7.53

EXAMPLE 9

ATTEMPTED REPETITION OF PIH AND RELATED COMPOUNDS DISCLOSED IN U.S. Pat. No. 2,810,725

Attempted synthesis of pyridoxal isonicotinoyl hydrazone (PIH) sulfate. Example 1 of U.S. Pat. No. 2,810,725

The experimental conditions of concentration, temperature and time are as disclosed Bernstein,in U.S. Pat. No. 2,810,725.

To a suspension of pyridoxine hydrochloride (0.05 Mol, 10.3 g) and manganese dioxide (0.05 Mol, 5.0 g) in 150 mL of water was added slowly 4.9 g (0.05 Mol) concentrated sulfuric acid. The resultant mixture was heated at 60°–70° C. for three hours. The reaction mixture was then cooled and filtered to remove the solids. Then 12.3 g sodium acetate and 6.85 g (0.05 Mol) iso-nicotinic acid hydrazide were added to the filtrate. The dark reddish brown solid that forms was left to stand overnight and was filtered off to give 1 5.0 g. After recrystallization from water the melting point was 230°–233° C. Analysis of the reddish brown precipitate, confirmed the presence of manganese as a 1:2 complex with PIH. Recrystallization from water again provided the same manganese complex of PIH.

Calculated for: $\{Mn \{C_{14}H_{14}N_4O_3\}_2 \cdot 8 H_2O\}$ Mn: 7.17; C: 43.70; H: 5.21; N: 14.60 Found: Mn: 7.41; C: 43.63; H: 4.68; N: 14.36

EXAMPLE 10

Attempted synthesis of pyridoxal isonicotinoyl hydrazone Example 2 of U.S. Pat. 2 810 725

The experimental conditions of concentration, temperature and time are as disclosed by Bernstein, in U.S. Pat. 2,810,725

A solution was made of the product obtained from Example 5 above, 3.35 g (0.01 Mol) in 20 cc 1 N hydrochloric acid. An orange-red precipitate appeared which, upon the addition of 20 cc of 0.5 N barium hydroxide (1.89 g) in water becomes a deep brown. The precipitate was filtered and to the filtrate was added 2.46 grams of sodium acetate which resulted in further precipitation of a small amount of brown solid. Further addition of acetic acid to the filtrate, produced no precipitate (of yellow or any other color). The brown precipitate obtained after the sodium acetate addition weighed 3.0 grams and proved to be a manganese complex of PIH (1:2). claimed:

Calculated for: $\{Mn (C_{14}H_{,14}N_4O_3)_2 \cdot 8 H_2O\}$ Mn: 7.17%; Found Mn: 7.23%

EXAMPLE 11

Attempted synthesis of pyridoxal isonicotinoyl hydrazone acid addition salts. Example 6 of U.S. Pat. 2,810,725 a): PIH(Mono) hydrochloride

Since Example 9 above did not yield PIH, analytically pure PIH was synthesized by the method of Sah supra. The synthesis of PIH (mono) hydrochloride was attempted under the experimental conditions of molar concentration disclosed in Example 6 of U.S. Pat. 2,810,725.

The disclosure calls for a solution of 57.2 mg pyridoxal isonicotinoyl hydrazone per 1 cc of absolute ethanol (28.6 g, 100 mMol in 500 cc) to which is then added an equimolar amount (100 mMol) of 4 N ethereal HCI.

This cannot be accomplished since the solubility of PIH in ethanol is approximately 1 mg/mL and would require a volume of 30,000 cc for dissolution as described and not 500 cc.

There was utilized a suspension that recreated the ratio of 57.2 mg PIH/cc abs ethanol (1.43 g, 5 mmole PIH in 25 cc absolute ethanol) to which was added one equivalent (5 mMol) of 4N ethereal HCI (1.25 cc) and stirred for one hour since no new precipitate is observed to occur upon addition of the ethereal HCI (as disclosed). The light orange solids were filtered to give 1.58 g. Attempts to recrystallize the solid thus obtained, "from a mixture of absolute ethanol and ether" was not possible since only 40 mg dissolved in 100 mL of ethanol (even upon heating). Addition of an equal volume of ether gave 30 mg of a light yellow solid which failed to yield an analysis for any known derivatives or solvates of PIH.

Calculated for PIH Hydrochloride ($C_{14}H_{14}N_4O_3 \cdot HCl$): C: 52.10 H: 4.68 N: 17.36 Cl: 10.98 Found C: 44.59 H: 5.31 N: 14:82 Cl: 11.11 b): Pyridoxal isonicotinoyl hydrazone dihydrochloride

Since Example 9 above did not yield PIH, analytically pure PIH was synthesized by the method of Sah supra. The synthesis of PIH dihydrochloride was attempted under the experimental conditions of molar concentration dis-closed in Example 6 of U.S. Pat. 2,810,725.

The disclosure calls for a solution of 28.6 mg pyridoxal isonicotinoyl hydrazone per 1 cc of absolute ethanol (28.6 g, 100 mMol in 500 cc) to which is then added a twice equimolar amount (200 mMol) of 4 N ethereal HCl.

This cannot be accomplished since the solubility of PIH in ethanol is approximately 1 mg/mL and would require a volume of 30.000 cc for dissolution as described and not 500 cc.

There was utilized a suspension of 57.2 mg/cc (1.43 g, 5 mMol in 25 cc absolute ethanol) to which were added two equivalents (10 mmoles) of 4 N ethereal HCl (2.5 cc) and stirred for one hour. The light yellow starting material became a copious off-white suspension. This was filtered and dried to give 1.68 g of a solid with melting point 250°–252° C. (dec) with discoloration beginning at 240° C. An authentic sample of PIH dihydrochloride, synthesized according to Example 1 supra, melts at 255°–257° C.

Following the procedure of U.S. Pat. 2,810,725 Bernstein, an attempt was made to recrystallize "from a mixture of acetonitrile and ether" which proved impossible since the solubility of the product in acetonitrile, even at a reduced scale, was so limited (less than 0.1 mg/mL) that addition of ether failed to reprecipitate any dissolved material.

PHARMACEUTICAL COMPOSITIONS

EXAMPLE 12
ENTERIC COATED GRANULE FORMULATION

| A) GRANULE COMPOSITION AS PERCENT BY WEIGHT: | |
|---|---|
| PIH · 2HCl (or other PIH · DPH) | 20–40% |
| Nonpareils (support spherules) 20/40 mesh | 60–80% |
| Povidone K32 | 5–10% |
| B) COMPOSITION OF ENTERIC COATING: | |
| Eudragit L-55/L-100 (enteric polymers) | 20–25% |
| Cellulose Acid Phthalate (enteric polymer) | 20–25% |
| Citro Flex A-2 (plasticizer) | 5–10% |
| Dibutyl Phthalate (plasticizer) | 5–10% |
| Talc Powder | 5–10% |
| Alcohol SDA 3C | to 100% |

C) PREPARATION OF THE LAYERED DRUG ON A SUPPORT COVERED BY AN ENTERIC COATING

The PIH.DPA drug is combined with sufficient ethanol to make it into a slightly damp thick paste which is further mixed with povidone and mechanically applied as a layered coating over a spherical support of defined mesh size. The supports themselves, if desired, are usually pharmacologically inactive, but an active support may also be utilized. The spherical matrix could be an acid resistant, biocompatible polymer. Examples are polycarbonate, polyethylene, teflon, microcrystalline cellulose, or other palstics. Other biocompatible polymers can also be used.

Enteric polymers and plasticizers are combined in ethanol to form a solution which is carefully sprayed over the support as a film which covers the active drug and protects it from premature dissolution in an environmental pH which is un-favorable for best absorption. The ensuing product is mechanically dried while preserving the uniformity of the enteric coating.

For example, utilizing a fluid bed coating method, it is possible to spray a solution containing from 1 kg to 100 kg of active material which than can be dried in serial batches. Larger equipment allows for up to 600 kg batches to be layered and dried.

EXAMPLE 13
ENTERIC COATED GRANULE FORMULATION (Preferred)*:

| A) GRANULE COMPOSITION | | Range (wt/wt %) |
|---|---|---|
| Batch Size | 7.0 Kg | |
| PIH · 2HCl (or other PIH · qDPH) | 1.75 Kg | 25.0% (20–30) |
| Povidone K32 | 0.645 Kg | 9.2% (8–10) |
| Nonpareils (support spherules) 20/40 mesh | 2.60 Kg | 37.1% (32–40) |
| Ethanol SDA 3C or SDA 3A | | |
| B) COMPOSITION OF ENTERIC COATING: | | |
| Eudragit L-55/L-100 (enteric polymers) | 1.32 Kg | 18.9% (15–25) |
| Acetyl triethylcitrate | 0.235 Kg | 3.4% (25–45) |
| Talc Powder | 0.445 Kg | 6.3% (55–70) |
| Alcohol SDA 3C or SDA 3A | 6.881 Kg | |

*Three Clinical Batches: Lot No. 920601 A1, 920602 A1, 920603 A1.

The enteric coatings are similarly applied using the same technology as in Example 12, for example ethanol, Povidone, PIH.2HCl are appropriately combined and diluted with further pharmaceutically acceptable alcohol and used to coat the nonpareils (beads). Proportionally larger amounts to 100 kg PIH.2HCl are readily prepared by this method.

The enteric layer preparation, for example, would consist of ethanol, acetyl triethylcitrate, Talc (USP), Eudragit L100, and the material appropriately diluted to a predetermined weight of 7.0 kg.

Proportionately larger batches to 199 kg are prepared in similar fashion with variation of the coating for degree of acid protection desired.

We claim:

1. A compound free of associated water, of the formula

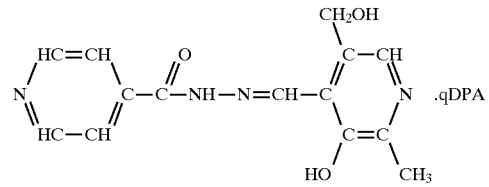

and the E and Z (transoid [anti] and cisoid [syn], respectively) isomers thereof, wherein q is ½,1 or 2, DPA is selected from the group consisting of sulfuric acid, phosphoric acid, ethanesulfonic acid, succinic acid, isethionic acid and nitric acid.

2. The compound of claim 1 wherein the DPA salt is dihydrogen sulfate, trihydrogen phosphate or dihydrogen ethanesulfonate.

3. The compound of claim 1 which is pyridoxal isonicotinoyl hydrazone di-(hydrogen ethanesulfonate).

4. Pyridoxal isonicotinoyl hydrazone hydrochloride tri-hemihydrate.

5. The compound of claim 1 which is pyridoxal isonicotinoyl hydrazone dihydrogen disuccinate.

6. The compound of claim 1 which is pyridoxal isonicotinoyl hydrazone di(hydrogen nitrate).

7. The compound of claim 1 which is pyridoxal isonicotinoyl hydrazone dihydrogen sulfate.

8. The compound of claim 1 which is pyridoxal isonicotinoyl hydrazone di(dihydrogen sulfate).

9. The compound of claim 1 which is pyridoxal isonicotinoyl hydrazone hemi (dihydrogen sulfate).

10. The compound of claim 1 which is pyridoxal isonicotinoyl hydrazone hydrogen isethionate.

11. A composition for reducing the level of iron in the cells of living subjects in need of such reduction comprising a reductively effective amount of a compound free of associated water, of the formula

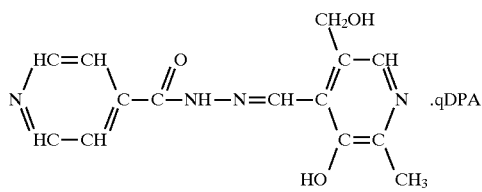

and the E and Z (transoid [anti] and cisoid [syn], respectively isomers thereof, wherein q is 1 or ½, DPA is selected from the group consisting of 2 mols of a monoprotic acid HX and 1 mol of a diprotic acid $H_2Y$ wherein X is a monovalent anion and Y is a divalent anion and both HX and $H_2Y$ are pharmaceutically acceptable acids and an orally administrable carrier.

12. The composition of claim 11 for reducing the level of iron in the cells of living subjects in need of such reduction wherein the reductively effective compound is pyridoxal isonicotinoyl hydrazone dihydrochloride.

13. The composition of claim 11 for reducing the level of iron in the cells of living subjects in need of such reduction wherein the orally administrable carrier is in a dosage form formulated for administration as enterically coated granules, tablets or capsules.

14. The composition of claim 13 for reducing the level of iron in the cells of living subjects in need of such reduction wherein the reductively effective compound is pyridoxal isonicotinoyl hydrazone dihydrochloride.

15. A method of for reducing the level of iron in the cells of living subjects in need of such reduction comprising administering to said subject a reductively effective amount of a compound free of associated water, of the formula

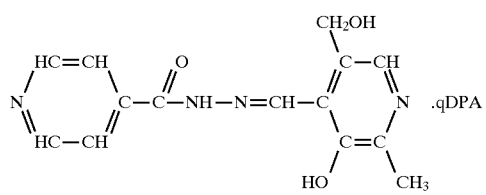

and the E and Z (transoid [anti] and cisoid [syn], respectively) isomers thereof, wherein q is ½ or 1, DPA is selected from the group consisting of 2 mols of a monoprotic acid HX and 1 mol of a diprotic acid $H_2Y$ wherein X is a monovalent anion and Y is a divalent anion and both HX and $H_2Y$ are pharmaceutically acceptable acids.

16. The method of claim 15 for reducing the level of iron in the cells of living subjects in need of such reduction the reductively effectively compound is pyridoxal isonicotinoyl hydrazone dihydrochloride.

17. The method of claim 15 for reducing the level of iron in the cells of living subjects in need of such reduction comprising administering to said subject said reductively effective compound in a dosage form formulated for administration as enterically coated granules, tablets or capsules.

18. The method of claim 17 for reducing the level of iron in the cells of living subjects in need of such reduction wherein the reductively effective compound is pyridoxal isonicotinoyl hydrazone dihydrochloride.

19. The method of claim 15 for reducing the level of iron in the cells of living subjects in need of such reduction additionally comprising administering to said subject sufficient pharmaceutically acceptable buffer to raise the pH of the stomach of said subject to a level of not less than about 3 and not more than about 8.

20. The method of claim 15 wherein the reductively effective agent is administered in the form of a powder.

21. The method of claim 19 for reducing the level of iron in the cells of living subjects in need of such reduction wherein the reductively effective compound is pyridoxal isonicotinoyl hydrazone dihydrochloride which is administered in conjunction with sufficient pharmaceutically acceptable buffer to raise the pH of the stomach of said subject to a level of not less than about 6 and not more than about 7.

* * * * *